United States Patent [19]

Hattori et al.

[11] Patent Number: 4,792,553

[45] Date of Patent: Dec. 20, 1988

[54] DIENE DERIVATIVES AND VASODILATORS CONTAINING THE SAME

[75] Inventors: Shin Hattori, Yokohama; Makoto Takai, Hachioji; Toshio Wakabayashi, Tama; Yasusi Suwabe, Kawasaki; Syozo Miyaoka, Tama, all of Japan

[73] Assignee: Terumo Kabushiki Kaisha, Tokyo, Japan

[21] Appl. No.: 10,477

[22] Filed: Feb. 3, 1987

[30] Foreign Application Priority Data

Feb. 4, 1986 [JP] Japan ................... 61-22506

[51] Int. Cl.$^4$ .................. A61K 31/495; C07D 295/06
[52] U.S. Cl. ..................... 514/255; 544/396
[58] Field of Search ................... 544/396; 514/255

[56] References Cited

U.S. PATENT DOCUMENTS 4,663,325  5/1987  Ohtaka et al. ................. 544/396

FOREIGN PATENT DOCUMENTS

| | | | |
|---|---|---|---|
| 152799 | 8/1985 | European Pat. Off. | 514/255 |
| 187639 | 7/1986 | European Pat. Off. | 514/255 |
| 189679 | 8/1986 | European Pat. Off. | 514/255 |
| 2139628 | 1/1973 | France | 514/255 |
| 9062489 | 6/1974 | Japan | 544/396 |
| 605873 | 10/1978 | Switzerland | 514/255 |

OTHER PUBLICATIONS

Takai et al., Chemical Abst. 106-156495h.

*Primary Examiner*—Donald G. Daus
*Assistant Examiner*—Cecilia Shen
*Attorney, Agent, or Firm*—Burns, Doane, Swecker & Mathis

[57] ABSTRACT

Novel dienyl derivatives are disclosed. As examples of said diene derivative are mentioned 1-benzhydryl-4-(5-phenyl-2,4-pentadienyl)piperazine, 1-(4,4'-difluorobenzhydryl)-4-(5-phenyl-2,4-pentadienyl)piperazine, 1-benzhydryl-4-(5-(3,4,5-trimethoxyphenyl)-2,4-pentadienyl)-piperazine, 1-(4,4'-difluorobenzhydryl)-4-(5-(2,4-dimethoxyphenyl)-2,4-pentadienyl)piperazine, 1-benzhydryl-4-(5-(2,3,4-trimethoxyphenyl)-2,4-pentadienyl)piperazine, 1-(4,4'-difluorobenzhydryl)-4-(5-(2,3,4-trimethoxyphenyl)-2,4-pentadienyl)piperazine and the like. These dienyl derivatives are useful as vasodilators.

23 Claims, No Drawings

DIENE DERIVATIVES AND VASODILATORS CONTAINING THE SAME

BACKGROUND OF THE INVENTION (1) Field of the Invention

The present invention relates to diene derivatives and vasodilators containing the same. The diene derivatives provided by the invention are novel compounds which possess a potent vasodilating activity. Therefore, they are effective for the therapy of vascular disturbances to be treated by increasing blood flow such as cerebrovascular, coronary vascular and peripheral vascular disturbances.

(2) Description of Prior Arts

Vascular disturbances observed with sequels of diseases such as cerebral infarction and myocardial infarction have become a greater portion of adult diseases in recent years. Development of drugs effectively preventing such diseases are highly desirable.

A large number of vasodilators including 3,4,5-trimethoxycinnamic acid derivatives have heretofore been developed, but they are not satisfactorily effective.

SUMMARY OF THE INVENTION

As a result of extensive studies on preparation of a variety of diene derivatives and their pharmacological activities, we have found that the diene derivatives according to the invention possess potent vasodilating activities. The present invention has been accomplished by the above finding.

Accordingly, an object of the invention is to provide diene derivatives represented by the general formula (I)

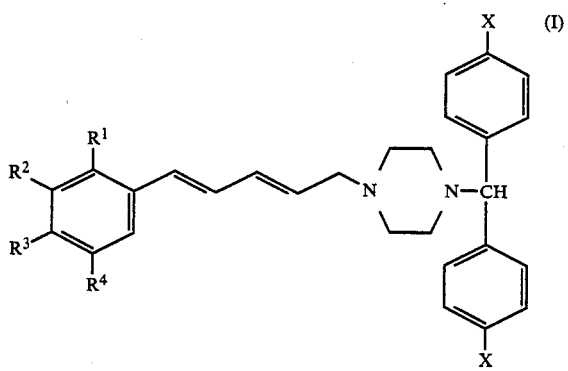

wherein $R^1$, $R^2$, $R^3$ and $R^4$ are the same or different and each represents a hydrogen atom, a hydroxyl group or a lower alkoxy group and X represents a hydrogen atom or a halogen atom.

A further object of the invention is to provide vasodilators containing a diene derivative represented by the above-mentioned general formula (I).

DETAILED DESCRIPTION OF THE INVENTION

In the definition of substituents of the above-mentioned formula (I), the lower alkoxy group means a straight or branched alkoxy group containing 1 to 4 carbon atoms and is preferably methoxy, ethoxy, n-propoxy, iso-propoxy, n-butoxy or the like. As the halogen atom is preferred chlorine, bromine or fluorine. Preferred combination of the groups is one in which all of $R^1$, $R^2$, $R^3$ and $R^4$ are hydrogen atoms, or $R^1$ is a hydrogen atom and $R^2$, $R^3$ and $R^4$ are lower alkoxy groups, preferably methoxy groups; or $R^1$ and $R^3$ are lower alkoxy groups, preferably methoxy groups and $R^2$ is a hydroxyl group and $R^4$ is a hydrogen atom; or $R^1$, $R^2$ and $R^3$ are lower alkoxy groups and $R^4$ is a hydrogen atom.

As preferred examples of the diene derivatives of the above-mentioned formula (I) are mentioned:
1-Benzhydryl-4-(5-phenyl-2,4-pentadienyl)piperazine,
1-(4,4'-difluorobenzhydryl)-4-(5-phenyl-2,4-pentadienyl)piperazine,
1-benzhydryl-4-(5-(3,4,5-trimethoxyphenyl)-2,4-pentadienyl)piperazine,
1-(4,4'-dichloro(or dibromo)benzhydryl)-4-(5-phenyl-2,4-pentadienyl)piperazine,
1-(4,4'-difluoro(or dichloro or dibromo)-benzhydryl)-4-(5-phenyl-2,4-pentadienyl)piperazine,
1-benzhydryl-4-(5-(3,4,5-triethoxyphenyl)-2,4-pentadienyl)piperazine,
1-benzhydryl-4-(5-(3,5-dimethoxy-4-hydroxy-phenyl)-2,4-pentadienyl)piperazine,
1-(4,4'-difluoro(or dichloro or dibromo)-benzhydryl)-4-(5-(3,5-dimethoxy-4-hydroxyphenyl)-2,4-pentadienyl)piperazine,
1-(4,4'-difluorobenzhydryl)-4-(5-(2,4-dimethoxyphenyl)-2,4-pentadienyl)piperazine,
1-benzhydryl-4-(5-(2,3,4-trimethoxyphenyl)-2,4-pentadienyl)piperazine, and
1-(4,4'-difluorobenzhydryl)-4-(5-(2,3,4-trimethoxyphenyl)-2,4-pentadienyl)piperazine.

The diene derivatives represented by the above-mentioned formula (I) are obtained by reacting reactive derivatives of carboxylic acids represented by the formula

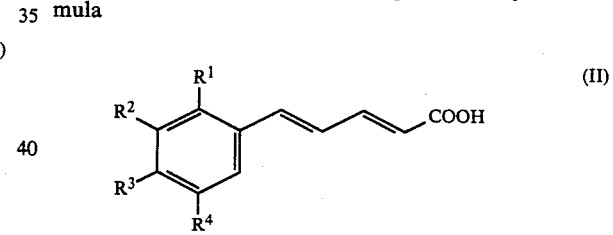

wherein $R^1$, $R^2$, $R^3$ and $R^4$ have the same meaning as defined above with an amine derivative represented by the formula (III)

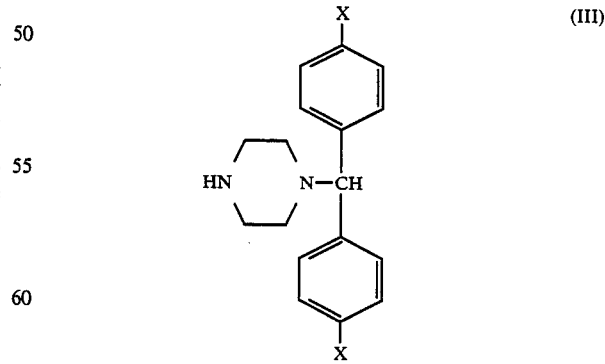

wherein X has the same meaning as defined above and then reducing the amido derivative, a reaction product.

The reaction derivative of the above-mentioned carboxylic acids (II) is preferably a halide, e.g., hydrochloride or bromide or an anhydride of said carboxylic acids. The reaction between the compound (II) and the compound (III) is carried out by a method known per se. For example, a reactive derivative of the carboxylic acids (II) is dissolved in an appropriate organic solvent, for example, chloroform, an amine derivative (III) is added to the solution, and the mixture is reacted for several hours at room temperature. After completion of the reaction, the desired product is isolated from the reaction mixture by a conventional method and is purified by such a means as column chromatography, if necessary. By reducing the amide product thus obtained by a reduction method known per se such as catalytic reduction or reduction with lithium aluminum hydride, there can be produced the dienyl derivatives (I). For example, the above-mentioned reduction reaction can be effected by dissolving the amide product in an appropriate organic solvent, for example, ether, adding lithium aluminum hydride to the solution and stirring the mixture. The desired product is isolated from the reaction mixture by a conventional method and purified by such a means as recrystallization or column chromatography.

The diene derivatives of the invention represented by the above-mentioned formula can, if desired, also be converted to an acid addition salt. The acid addition salts thus produced are also covered by the scope of the invention. As the preferred acid addition salt are mentioned those with a mineral acid, for example, hydrochloric acid, sulfuric acid or the like or with an organic acid such as acetic acid, maleic acid, fumaric acid, malic acid or the like.

The diene derivatives of the invention are effective for the use as vasodilators which are used for the treatment of diseases such as cerebrovascular disturbances, coronary vascular disturbances and peripheral vascular disturbances. The dosage is usually 50–1500 mg per day in adults which may be divided into 1–3 doses, as needed.

Oral administration is the desirable method of administration, and intravenous administration is also applicable.

The diene derivatives of the invention in admixture with pharmaceutical carriers or excipients are formed into tablets, powders, capsules or granules. As examples of the carrier or excipient are mentioned calcium carbonate, calcium phosphate, starch, sucrose, lactose, talc, magnesium stearate and the like. The piperazine derivatives of the invention can also be formed into liquid preparations such as oily suspension, syrup and injectable preparations.

Examples and results of a general test to confirm the vasodilating activities and an acute toxicity test are given below to describe the invention in more details.

EXAMPLE 1

To 2.71 g (56.5 mmol) of 50% sodium hydride, washed with anhydrous tetrahydrofuran in the atmosphere of argon, was added 150 ml of anhydrous tetrahydrofuran. To the mixture, cooled to 0° C., was added dropwise a solution of 14.15 g (56.5 mmol) of triethyl-4-phosphocrotonate dissolved in 25 ml of anhydrous tetrahydrofuran through a dropping funnel over 10 minutes. After 30 min., a solution of 4.00 g (37.7 mmol) of benzaldehyde dissolved in 25 ml of anhydrous tetrahydrofuran was added dropwise through a dropping funnel over 10 minutes. Temperature of the reaction mixture was raised from 0° C. to room temperature followed by stirring for 17 hours. To the resulting mixture were successively added saturated aqueous solution of ammonium chloride and water followed by extraction with benzene. The organic layer was washed three times with water, then dried over anhydrous sodium sulfate and concentrated under reduced pressure. There was obtained 10.10 g of a residue. It was subjected to column chromatography on silica, and from the benzene eluate fraction was produced 3.72 g (18.4 mmol) of ethyl 5-phenyl-2,4-pentadienoate.

To 3.72 g (18.4 mmol) of said ethyl 5-phenyl-2,4-pentadienoate was added 40 ml of methanol to give a solution. To the solution was then added a solution of 7.40 g (184 mmol) of sodium hydroxide dissolved in 10 ml of water, and the mixture was stirred at room temperature for 1 hour. The resulting mixture was concentrated under reduced pressure followed by addition of water and a hydrochloric acid solution to adjust the pH to 1 and extraction with chloroform. The organic layer was washed with water and then dried over anhydrous sodium sulfate. Concentration under reduced pressure gave 3.10 g of a residue. Recrystallization from ethanol yielded 1.12 g (6.43 mmol) of 5-phenyl-2,4-pentadienoic acid.

To 1.00 g (5.74 mmol) of 5-phenyl-2,4-pentadienoic acid were added 60 ml of dry dichloromethane and 0.80 ml (5.74 mmol) of triethylamine in the atmosphere of argon. The mixture was stirred at 0° C. followed by addition of 0.55 ml (5.74 mmol) of ethylcarbonyl chloride. The resulting mixture was stirred for 1 hour followed by addition of 1.74 g (6.89 mmol) of benzhydrylpiperazine. Temperature of the mixture was raised to room temperature followed by stirring for additional 30 min., addition of chloroform and successive extractions with aqueous hydrochloric acid solution (pH=1), saturated aqueous solution of sodium hydrogen carbonate and water. The organic layer was dried over anhydrous sodium sulfate and concentrated under reduced pressure. There was obtained 2.50 g of a residue. Column chromatography on silica gel and recrystallization from ethanol of the benzene-ethyl acetate (10 : 1) fraction yielded 1.26 g (3.08 mmol) of 1-benzhydryl-4-(5-phenyl-2,4-pentadienoyl)piperazine.

To 1.25 g (3.06 mmol) of said 1-benzhydryl-4-(5-phenyl-2,4-pentadienoyl)piperazine was added 50 ml of dry ether, and the mixture was stirred. After slow addition of 87 mg (2.29 mmol) of lithium aluminum hydride, the mixture was stirred for 30 min. under spontaneous reflux. To the reaction mixture were added saturated aqueous solution of ammonium chloride and water, and the mixture was extracted with chloroform. The organic layer was successively washed with aqueous hydrochloric acid solution (pH=1), saturated sodium hydrogen carbonate solution and water, dried over anhydrous sodium sulfate and concentrated under reduced pressure. There was obtained 1.07 g of a residue. Column chromatography on silica gel and recrystallization from ethanol of the fraction eluted with benzene-ethyl acetate (10 : 1) yielded 0.16 g (0.41 mmol) of 1-benzhydryl-4-(5-phenyl-2,4-pentadienyl)piperazine. Spectrophotometric data of the product support the structure (IV).

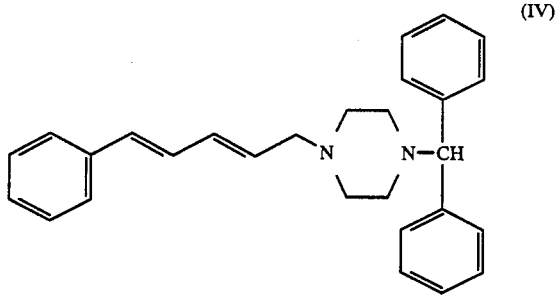

(IV)

NMR (60 MHz, CDCl$_3$), δ: 7.57~5.65(19 H, m), 4.23 (1H, s), 3.07 (2H, d, J=6 Hz), 2.70~2.40 (8H, m).
IR$\nu^{cm-1}$: 2800, 1490, 1450, 980, 705.

EXAMPLE 2

To 5.00 g (22.7 mmol) of 4,4'-difluorobenzhydrol was added 16.5 ml (227 mmol) of thionyl chloride in the atmosphere of argon, and the mixture was stirred at room temperature for 30 minutes. To the resulting mixture was added water followed by extraction with benzene. The organic layer was successively washed with saturated sodium hydrogen carbonate solution and water, dried over anhydrous sodium sulfate and concentrated under reduced pressure. The residue thus obtained was subjected to column chromatography on silica gel. There was yielded 4.90 g (20.5 mmol) of 4,4'-difluorobenzhydryl chloride from the fraction eluted with benzene.

To 4.90 g (20.5 mmol) of said 4,4'-difluorobenzhydryl chloride were 4.26 g (30.8 mmol) of anhydrous potassium carbonate, 8.83 g (102.5 mmol) of piperazine and 200 ml of dry chloroform, and the mixture was heated under reflux for 18 hours. The reaction mixture was washed twice with water, and the organic layer was dried over anhydrous sodium sulfate and concentrated under reduced pressure. There was obtained 6.11 g of a residue. It was subjected to column chromatography on silica gel, and the chloroform-methanol (20:1) fraction yielded 2.77 g (9.64 mmol) of 4,4'-difluorobenzhydrylpiperazine.

To 500 mg (2.87 mmol) of 5-phenyl-2,4-pentadienoic acid were added 30 ml of dry dichloromethane and 0.40 ml (2.87 mmol) of triethylamine, and the mixture was stirred at 0° C. To the resulting mixture was added 0.28 ml (92.87 mmol) of ethylcarbonyl chloride followed by stirring for 1 hour. To the mixture was added 1.00 g (3.48 mmol) of 4,4'-difluorobenzhydrylpiperazine. Temperature of the mixture was raised to room temperature followed by stirring for additional 30 min., addition of chloroform and successive extractions with aqueous hydrochloric acid solution, saturated aqueous solution of sodium hydrogen carbonate and water. The organic layer was dried over anhydrous sodium sulfate and concentrated under reduced pressure. There was obtained 1.42 g of a residue. It was subjected to column chromatography on silica gel, and the benzeneethyl acetate (20:1) fraction yielded 760 mg (1.71 mmol) of 1-(4,4'-difluorobenzhydryl)-4-(5-phenyl-2,4-pentadienoyl)piperazine.

To 760 mg (1.71 mmol) of said 1-(4,4'-difluorobenzhydryl)-4-(5-phenyl-2,4-pentadienoyl)piperazine was added 30 ml of dry ether, and the mixture was stirred. After slow addition of 49 mg (1.28 mmol) of lithium aluminum hydride, the mixture was stirred for 30 min. under spontaneous reflux. To the reaction mixture were added saturated aqueous solution of ammonium chloride and water followed by extraction with chloroform. The organic layer was successively washed with aqueous hydrochloric acid solution (pH=1), saturated sodium hydrogen carbonate solution and water, dried over anhydrous sodium sulfate and concentrated under reduced pressure. There was obtained 500 mg of a residue. It was subjected to column chromatography on silica gel, and the fraction eluted with benzene-ethyl acetate (10:1) yielded 240 mg (0.53 mmol) of 1-(4,4'-difluorobenzhydryl)-4-(5-phenyl-2,4-pentadienyl)piperazine. Spectrophotometric data of the product support the structure (V).

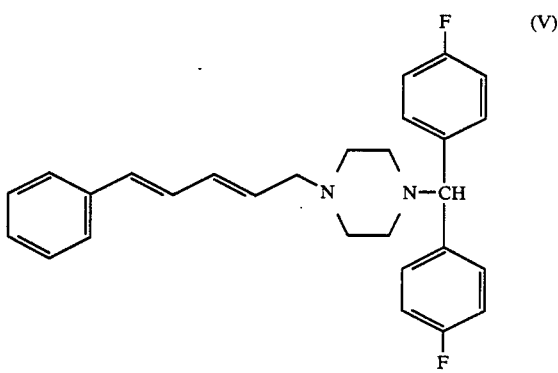

(V)

NMR (60 MHz, CDCl$_3$), δ: 7.50~5.50(17H, m), 4.16 (1H, s), 3.04 (2H, d, J=6 Hz), 2.70~2.20 (8H, m).
IR$\nu^{cm-1}$: 2800, 1600, 1500, 1220, 820.

EXAMPLE 3

To 500 mg (1.89 mmol) of 5-(3,4,5-trimethoxyphenyl)-2,4-pentadienoic acid were added 20 ml of dry dichloromethane and 0.27 ml (1.89 mmol) of triethylamine in the atmosphere of argon, and the mixture was stirred at 0° C. To the resulting mixture was added 0.18 ml of ethylcarbonyl chloride followed by stirring for 1 hour and addition of 572 mg (2.27 mmol) of benzhydrylpiperazine. Temperature of the mixture was raised to room temperature followed by stirring for additional 30 min., addition of chloroform and successive extractions with aqueous hydrochloric acid solution (pH=1), saturated aqueous solution of sodium hydrogen carbonate and water. The organic layer was dried over anhydrous sodium sulfate and concentrated under reduced pressure. There was obtained 904 mg of a residue. Recrystallization from a benzene-ethyl acetate (10:1) solvent yielded 655 mg (1.31 mmol) of 1-benzhydryl-4-(5-(3,4,5-trimethoxyphenyl)-2,4-pentadienoyl)piperazine.

To 655 mg (1.31 mmol) of said 1-benzhydryl-4-(5-(3,4,5-trimethoxyphenyl)-2,4-pentadienoyl)piperazine was added 20 ml of dry ether followed by stirring. After slow addition of 37 mg (0.99 mmol) of lithium aluminum hydride, the mixture was stirred for 30 min. under spontaneous reflux. The reaction mixture, after addition of saturated aqueous solution of ammonium chloride and water, was extracted with chloroform. The organic layer was then washed successively with aqueous hydrochloric acid solution (pH=1), saturated sodium hydrogen carbonate solution and water, dried over anhydrous sodium sulfate and concentrated under reduced pressure. There was obtained 560 mg of a residue. It was subjected to column chromatography on silica gel, and the fraction eluted with chloroform yielded 210 mg (0.43 mmol) of 1-benzhydryl-4-(5-(3,4,5-trimethoxyphenyl)-2,4-pentadienyl)piperazine. Spectrophotometric data of the product support the structure (VI).

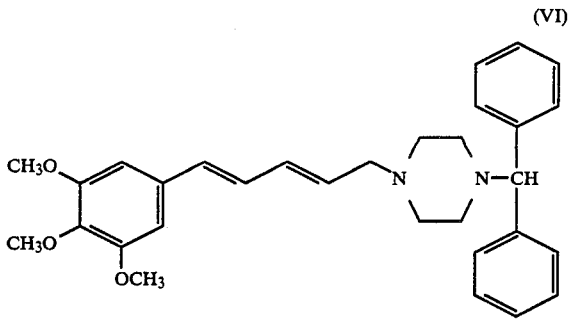

(VI)

NMR (60 MHz, CDCl₃), δ: 7.57~5.65(16H, m), 4.23 (1H, s), 3.83 (9H, s), 3.08 (2H, d, J=6 Hz), 2.70~2.20 (8H, m).

IRν$^{cm-1}$: 2800, 1580, 1510, 1025, 1005, 705.

EXAMPLE 4

To 9.00 g (72.2 mmol) of 50% potassium butoxide, 200 ml of anhydrous tetrahydrofuran was added in the atmosphere of argon. To the mixture, cooled to 0° C., was added dropwise a solution of 25.81 g (72.2 mmol) of triethyl-4-phosphocrotonate dissolved in 30 ml of anhydrous tetrahydrofuran through a dropping funnel over 30 minutes. After 30 min., a solution of 10 g (60.2 mmol) of 2,4-dimethoxybenzaldehyde dissolved in 30 ml of anhydrous tetrahydrofuran was added dropwise through a dropping funnel over 10 minutes. Temperature of the reaction mixture was raised from 0° C. to room temperature followed by stirring for 18 hours. To the resulting mixture were successively added saturated aqueous solution of ammonium chloride and water followed by extraction with ethyl acetate. The organic layer was washed with water and saturated aqueous solution of ammonium chloride, then dried over anhydrous magnesium sulfate and concentrated under reduced pressure to obtain a residue. It was subjected to column chromatography on silica, and from the ethyl acetate-hexane (1:7) eluate fraction was produced 9.44 g (36.0 mmol) of ethyl 5-(2,4-dimethoxyphenyl)-2,4-pentadienoate.

To 9.44 g (36.0 mmol) of said ethyl 5-(2,4-dimethoxyphenyl)-2,4-pentadienoate was added 80 ml of methanol to give a solution. To thesolution was then added a solution of 14.40 g (360 mmol) of sodium hydroxide dissolved in 20 ml of water, and the mixture was stirred at room temperature for 2 hours. The resulting mixture was concentrated under reduced pressure followed by addition of water and a hydrochloric acid solution to adjust the pH to 1 and extraction with chloroform. The organic layer was washed with water and a saturated aqueous sodium chloride solution and then dried over anhydrous magnesium sulfate. Concentration under reduced pressure gave 7.70 g (32.9 mmol) of 5-(2,4-dimethoxyphenyl)-2,4-pentadienoic acid.

To 15.0 g (68.1 mmol) of 4,4'-difluorobenzhydrol was added 14.9 ml (204 mmol) of thionyl chloride in the atmosphere of argon, and the mixture was stirred at room temperature for 30 minutes. To the resulting mixture was added water followed by extraction with benzene. The organic layer was successively washed with water, dried over anhydrous sodium sulfate and concentrated under reduced pressure. The residue thus obtained was subjected to column chromatography on silica gel. There was yielded 14.32 g (60 mmol) of 4,4'-difluorobenzhydryl chloride from the fraction eluted with benzene.

To 14.32 g (60 mmol) of said 4,4'-difluorobenzhydryl chloride were added 10.46 g (90 mmol) of anhydrous sodium carbonate, 25.84 g (300 mmol) of piperazine and 52 ml of dry chloroform, and the mixture was heated under reflux. To the reaction mixture was added dropwise over 45 minutes 14.32 g (60 mmol) of 4,4'-difluorobenzhydryl chloride in 13 ml of dry chloroform. The mixture was heated under reflux for 18 hours and filtered. The filtrate was washed successively with water and a saturated aqueous sodium chloride solution, and the organic layer was dried over anhydrous sodium sulfate and concentrated under reduced pressure. There was obtained a residue, which was subjected to column chromatography on silica gel to give 13.49 g (47 mmol) of 4,4'-difluorobenzhydryl piperazine from eluates of dichloromethane-methanol (10:1).

To 7.50 g (32.0 mmol) of 5-(2,4-dimethoxyphenyl)-2,4-pentadienoic acid were added 300 ml of dry dichloromethane and 4.46 ml (32.0 mmol) of triethylamine in the atmosphere of argon. The mixture was stirred at 0° C. followed by addition of 3.06 ml (32.0 mmol) of ethylcarbonyl chloride. The resulting mixture was stirred for 1 hour followed by addition of 11.04 g (38.4 mmol) of 4,4'-difluorobenzhydrylpiperazine in 50 ml of dry dichloromethane. Temperature of the mixture was raised to room temperature followed by stirring for additional 16 hours. After addition of water, the mixture was extracted with dichloromethane. The organic layer was washed successively with aqueous 1N-hydrochloric acid solution, a saturated aqueous solution of sodium chloride and a saturated aqueous solution of sodium hydrogen carbonate and a saturated aqueous solution of sodium chloride. The organic layer was dried over anhydrous magnesium sulfate and concentrated under reduced pressure. There was obtained a residue, which was subjected to column chromatography on silica gel to give 11.9 g (23.6 mmol) of 1-(4,4'-difluorobenzhydryl)-4-(5-(2,4-dimethoxyphenyl)-2,4-pentadienoyl)piperazine from eluate of ethyl acetate-hexane (1:1).

To 11.6 g (23.0 mmol) of said 1-(4,4'-difluorobenzhydryl)-4-(5-(2,4-dimethoxyphenyl)-2,4-pentadienoyl)piperazine was added 250 ml of dry ether, and the mixture was stirred. After slow addition of 870 mg (23.0 mmol) of lithium aluminum hydride, the mixture was heated for 1 hour under reflux. To the reaction mixture was added saturated aqueous solution of ammonium chloride, and the mixture was extracted with ether. The organic layer was washed with a saturated sodium chloride solution, dried over anhydrous magnesium sulfate and concentrated under reduced pressure. There was obtained a residue, which was subjected to column chromatography on silica gel and eluted with chloroform-methanol (40:1) to give 9.50 g (19.4 mmol) of 1-(4,4'-difluorobenzhydryl)-4-(5-(2,4-dimethoxyphenyl)-2,4-pentadienyl)piperazine. Spectrophotometric data of the product support the structure (VII).

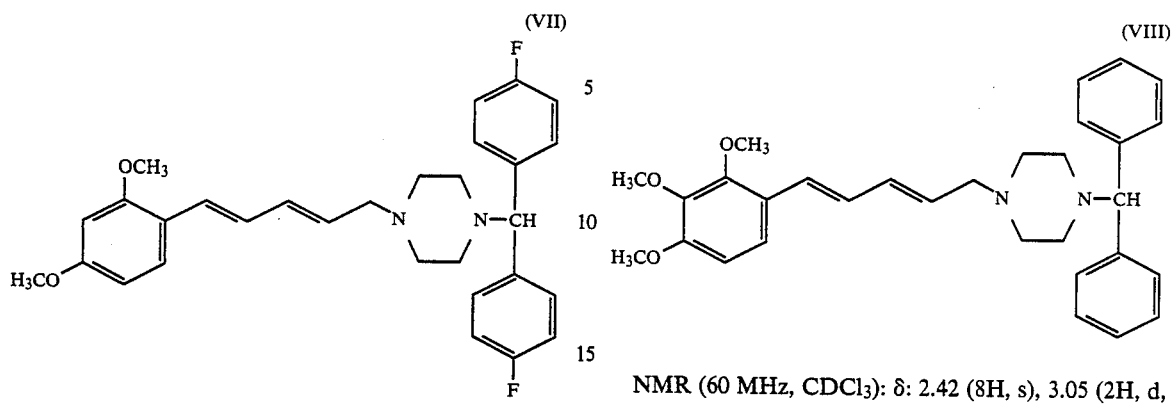

NMR (60 MHz, CDCl₃), δ: 2.43 (8H, s), 3.05 (2H, d, J=6 Hz), 3.75 (6H, s), 4.20 (1H, s), 5.45–7.48 (15H, m),
IR$\nu^{cm-1}$ (CHCl₃): 2810, 1605, 1505, 1160, 990.

NMR (60 MHz, CDCl₃): δ: 2.42 (8H, s), 3.05 (2H, d, J=6 Hz), 3.82 (9H, s), 4.22 (1H, s), 5.45–7.51 (16H, m).
IR$\nu^{cm-1}$ (CHCl₃): 2805, 1495, 1460, 1300, 1095, 705.

EXAMPLE 5

To 7.3 g (27.6 mmol) of 5-(2,3,4-trimethoxyphenyl)-2,4-pentadienoic acid were added 300 ml of dry dichloromethane and 3.85 ml (27.6 mmol) of triethylamine, and the mixture was stirred at 0° C. To the resulting mixture was added 2,64 ml (27,6 mmol) of ethylcarbonyl chloride followed by stirring for 1 hour. To the mixture was added 8.36 g (33 mmol) of benzhydrylpiperazine in 50 ml of dry dichloromethane. Temperature of the mixture was raised to room temperature followed by stirring for additional 16 hours. After addition of water, the mixture was extracted with dichloromethane. The organic layer was washed successively with aqueous 1N-hydrochloric acid solution, a saturated aqueous sodium chloride solution and a saturated aqueous sodium hydrogen carbonate solution and a saturated aqueous sodium chloride solution. The organic layer was dried over anhydrous magnesium sulfate and concentrated under reduced pressure. There was obtained a residue, which was subjected to column chromatography on silica gel to give 10.0 g (20.1 mmol) of 1-benzhydryl-4-(5-(2,3,4-trimethoxyphenyl)-2,4-pentadienoyl)piperazine from eluates of ethyl acetate-hexane (1:1).

To 10.0 g (20.1 mmol) of said 1-benzhydryl-4-(5-(2,3,4-trimethoxyphenyl)-2,4-pentadienoyl)piperazine was added 250 ml of dry ether, and the mixture was stirred. After addition of 760 mg (20.1 mmol) of lithium aluminum hydride, the mixture was heated under reflux for 1 hour To the reaction mixture were added a saturated aqueous solution of ammonium chloride followed by extraction with ether. The organic layer was washed with a saturated aqueous sodium chloride solution, dried over anhydrous magnesium sulfate and concentrated under reduced pressure There was obtained a residue, which was subjected to column chromatography on silica gel to give 9.40 g (19.4 mmol) of 1-benzhydryl-4-(5-(2,3,4-trimethoxyphenyl)-2,4-pentadienyl)-piperazine. Spectrophotometric data of the product support the structure (VIII).

EXAMPLE 6

7.30 g (27.6 mmol) of 5-(2,3,4-trimethoxyphenyl)-2,4-pentadienoic acid was dissolved in 300 ml of dry dichloromethane and 3.85 ml (27.6 mmol) of triethylamine was added thereto in the atmosphere of argon, and the mixture was stirred at 0° C. To the resulting mixture was added 2.64 ml (27.6 mmol) of ethylcarbonyl chloride followed by stirring for 1 hour and adding 9.59 g (33 mmol) of 4,4'-difluorobenzhydrylpiperazine in 50 ml of dry dichloromethane. Temperature of the mixture was raised to room temperature followed by stirring for additional 16 hours. After addition of water, the mixture was extracted with dichloromethane. The organic layer was washed successively with aqueous 1N-hydrochloric acid solution, a saturated aqueous sodium chloride solution, a saturated aqueous hydrogen carbonate solution and a saturated aqueous sodium chloride solution. The organic layer was dried over anhydrous magnesium sulfate and concentrated under reduced pressure. There was obtained a residue, which was subjected to column chromatography on silica gel to give 10.6 g (20 mmol) of 1-(4,4'-difluorobenzhydryl)-4-(5-(2,3,4-trimethoxyphenyl)-2,4-pentadienoyl)piperazine from eluates of ethyl acetate-hexane (1:1).

10.6 g (20 mmol) of said 1-(4,4' difluorobenzhydryl)-4-(5-(2,3,4-trimethoxyphenyl)-2,4,-pentadienoyl)piperazine was dissolved in 250 ml of dry ether. After addition of 760 mg (20.1 mmol) of lithium aluminum hydride, the mixture was heated under reflux for 1 hour. The reaction mixture, after addition of saturated aqueous solution of ammonium chloride, was extracted with ether. The organic layer was then washed with a saturated sodium chloride solution, dried over anhydrous magnesium sulfate and concentrated under reduced pressure. There was obtained a residue, which was subjected to column chromatography on silica gel to give 9.8 g (19 mmol) of 1-(4,4'-difluorobenzhydryl)-4-(5-(2,3,4-trimethoxyphenyl)-2,4-pentadienyl)piperazine from eluates of chloroform-methanol (40:1). Spectrophotometric data of the product support the structure (IX).

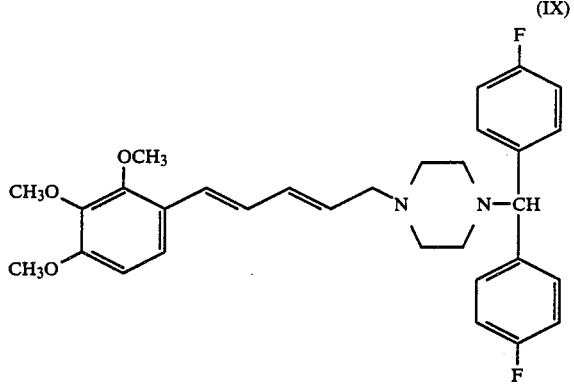

(IX)

NMR (60 MHz, CDCl$_3$), δ: 2.42 (8H, s), 3.05 (2H, d, J=6 Hz), 3.80 (9H, s), 4.20 (1H, s), 5.40–7.50 (14H, m), IRνcm$^{-1}$ (CHCl$_3$): 2810, 1600, 1505, 1160.

TEST EXAMPLE (VASODILATING ACTIVITY)

Mixed breed adult dogs weighing around 10 kg were anesthesized with sodium pentobarbital (30 mg/kg, i.v.) and undergone self perfusion of the left femoral artery under artificial respiration. Blood flow in the left femoral artery was measured by means of a surgical probe. A diene derivative to be tested dissolved in a 5% ethanol solution was administered through the femoral artery. The results demonstrated vasodilating activities by increasing blood flow in the femoral artery without the effect on blood pressure. Percent increase in blood flow in the femoral artery by the administration of typical examples of said diene derivative in comparison with the one prior to the administration is given in Table 1. Sinepazid (1-[(1-pyrrolidinylcarbonyl)methyl]-4-(3,4,5-trimethoxycinnamoyl)piperazine) was employed as a control drug.

TABLE I

| | Vasodilating activity | | |
|---|---|---|---|
| Test compound | Ex. No. | Dose (mg/kg, arterial) | Percent increase in blood flow in the femoral artery (%) |
| [structure] | 1 | 0.1<br>0.3<br>1.0<br>3.0 | 14.3<br>18.2<br>43.5<br>170.8 |
| [structure] | 2 | 0.1<br>0.3<br>1.0<br>3.0 | 9.5<br>14.3<br>24.0<br>84.0 |
| [structure] | 3 | 0.1<br>0.3<br>1.0<br>3.0 | 20.0<br>36.0<br>115.4<br>196.0 |

TABLE I-continued

Vasodilating activity

| Test compound | Ex. No. | Dose (mg/kg, arterial) | Percent increase in blood flow in the femoral artery (%) |
|---|---|---|---|
| [2,4-dimethoxyphenyl diene piperazine with 4-F,4-F-benzhydryl] | 4 | 0.1<br>0.3<br>1.0<br>3.0 | 15<br>30<br>100<br>165 |
| [2,3,4-trimethoxyphenyl diene piperazine with benzhydryl] | 5 | 0.1<br>0.3<br>1.0<br>3.0 | 18<br>35<br>110<br>180 |
| [2,3,4-trimethoxyphenyl diene piperazine with 4-F,4-F-benzhydryl] | 6 | 0.1<br>0.3<br>1.0<br>3.0 | 20<br>40<br>120<br>190 |
| Sinebazid | — | 0.1<br>0.3<br>1.0<br>3.0 | 11<br>19<br>54<br>99 |

(Acute Toxicity)

An acute toxicity test was made in ICR male mice (5 weeks old) by oral administration. $LD_{50}$ values were 400 mg/kg or higher for all the tested diene derivatives of the invention thereby demonstrating high safety because of far larger amount than effective dose.

What is claimed is:

1. A diene compound represented by the formula

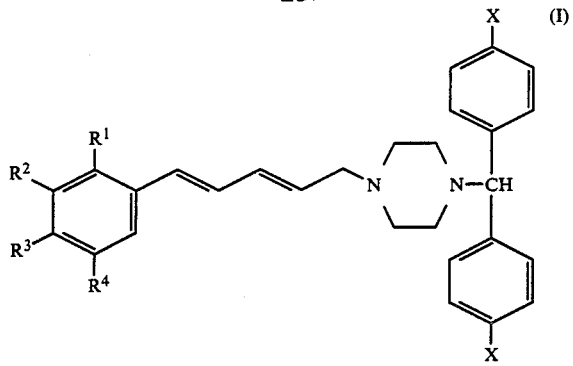

wherein $R^1$, $R^2$, $R^3$ and $R^4$ are the same or different and each represents a hydrogen atom or a $C_1$-$C_4$ alkoxy group, and X represents a hydrogen atom or a halogen atom.

2. A diene compound according to claim 1 wherein $R^1$, $R^2$, $R^3$, and $R^4$ are all hydrogen atoms.

3. A diene compound according to claim 1 wherein $R^1$ is a hydrogen atom and $R^2$, $R^3$ and $R^4$ are $C_1$-$C_4$ alkoxy groups.

4. A diene compound according to claim 3 wherein the $C_1$-$C_4$ alkoxy groups are methoxy groups.

5. A diene compound according to claim 1 wherein $R^1$, $R^2$ and $R^3$ are lower alkoxy groups and $R^4$ is a hydrogen atom.

6. A diene compound according to claim 5 wherein the $C_1$-$C_4$ alkoxy groups are methoxy groups.

7. A diene compound according to claim 1 wherein $R^1$ and $R^3$ are $C_1$-$C_4$ alkoxy groups and $R^2$ and $R^4$ are hydrogen atoms.

8. A diene compound according to claim 7 wherein the $C_1$-$C_4$ alkoxy groups are methoxy groups.

9. A diene compound according to claim 1 wherein X is fluorine.

10. A pharmaceutical composition for treating cetebrovascular, coronary vascular or peripheral vascular disturbances said composition comprising a sufficient amount of a diene comound represented by the formula

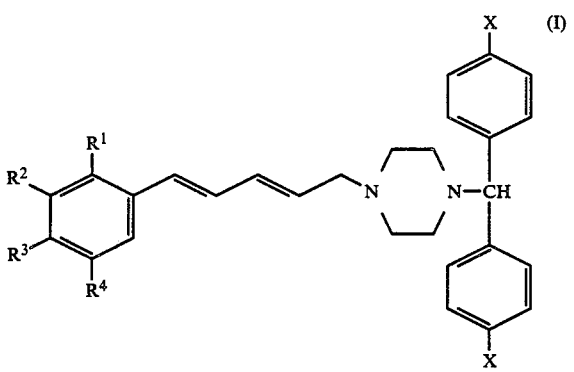

wherein $R^1$, $R^2$, $R^3$ and $R^4$ are the same or different and each represents a hydrogen atom or a $C_1$-$C_4$ alkoxy group and X represents a hydrogen atom or a halogen atom, to treat cerebrovascular, coronary vascular or peripheral vascular disturbances and a pharamaceutically acceptable carrier.

11. The pharmaceutical composition according to claim 10 wherein $R^1$, $R^2$, $R^3$ and $R^4$ are all hydrogen atoms.

12. The pharamaceutical composition according to claim 10 wherein $R^1$ is a hydrogen atom and $R^2$, $R^3$ and $R^4$ are $C_1$-$C_4$ alkoxy groups.

13. The pharmaeutical composition according to claim 10 wherein $R^1$, $R^2$ and $R^3$ are $C_1$-$C_4$ alkoxy groups and $R^4$ is a hydrogen atom.

14. The pharmacuetical composition according to claim 10 wherein $R^1$ and $R^3$ are $C_1$-$C_4$ alkoxy groups and $R^2$ and $R^4$ are hydrogen atoms.

15. The pharmaceutical composition according to claim 10 wherein X is fluorine.

16. The pharmaceutical composition according to claim 10 comprising 50-1500 mg per day of the diene compound.

17. A method for treating cerebrovascular, coronary vascular or peripheral vascular disturbances in a mammalian organism comprising administering to a mammalian organism in need of such treatment a sufficient amount of a diene compound represented by the formula

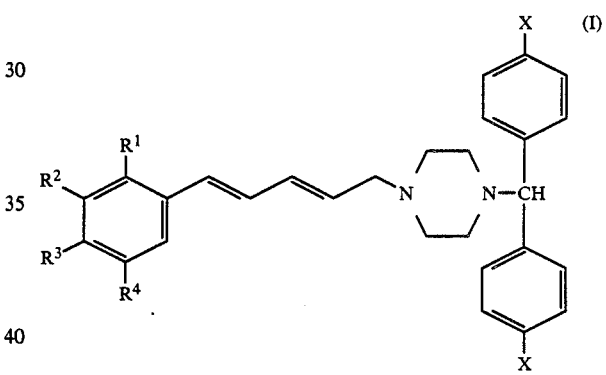

wherein $R^1$, $R^2$, $R^3$ and $R^4$ are the same or different and each represents a hydrogen atom or a $C_1$-$C_4$ alkoxy group, and X represents a hydrogen atom or a halogen atom.

18. The method according to claim 17 wherein $R^1$, $R^2$, $R^3$ and $R^4$ are all hydrogen atoms.

19. The method according to claim 17 wherein $R^1$ is a hydrogen atom and $R^2$, $R^3$ and $R^4$ are $C_1$-$C_4$ alkoxy groups.

20. The method according to claim 17 wherein $R^1$, $R^2$ and $R^3$ are $C_1$-$C_4$ alkoxy groups and $R^4$ is a hydrogen atom.

21. The method according to claim 17 wherein $R^1$ and $R^3$ are $C_1$-$C_4$ alkoxy groups and $R^2$ and $R^4$ are hydrogen atoms.

22. The method according to claim 17 wherein X is fluorine.

23. A method according to claim 17 wherein the effective dose is 50-1500 mg per day in adults.

* * * * *